(12) United States Patent
Choi et al.

(10) Patent No.: US 12,004,548 B2
(45) Date of Patent: Jun. 11, 2024

(54) METHOD FOR PRODUCING BLACK GINSENG CONCENTRATE WITH INCREASED PROSAPOGENIN GINSENOSIDE CONTENT USING CONTINUOUS STEAMING-DRYING TECHNIQUE AND COMBINED CONCENTRATION TECHNOLOGY

(71) Applicant: DAEDONG KOREA GINSENG CO., LTD, Chungcheongnam-do (KR)

(72) Inventors: Sung-Keun Choi, Chungcheongnam-do (KR); Sung Soo Jang, Chungcheongnam-do (KR); Chang-Soon Lee, Chungcheongbuk-do (KR); Byeong-Seon Jeon, Daejeon (KR); Kun Hee Lee, Daejeon (KR); Kyung Su Lee, Daejeon (KR); Han Sol Lee, Chungcheongbuk-do (KR); Hye Jeong Jeon, Daejeon (KR); Byoung Man Kong, Daejeon (KR)

(73) Assignee: DAEDONG KOREA GINSENG CO., LTD, Chungcheongnam-Do (KR)

( * ) Notice: Subject to any disclaimer, the term of this patent is extended or adjusted under 35 U.S.C. 154(b) by 91 days.

(21) Appl. No.: 17/868,959

(22) Filed: Jul. 20, 2022

(65) Prior Publication Data
US 2023/0255244 A1 Aug. 17, 2023

(30) Foreign Application Priority Data
Feb. 11, 2022 (KR) ........................ 10-2022-0017912

(51) Int. Cl.
*A23L 5/00* (2016.01)
*A23L 5/10* (2016.01)
(Continued)

(52) U.S. Cl.
CPC ................. *A23L 5/51* (2016.08); *A23L 5/13* (2016.08); *A23L 19/10* (2016.08); *A23L 33/105* (2016.08); *B01D 1/0082* (2013.01)

(58) Field of Classification Search
CPC ........... A23L 19/10; A23L 5/13; A23L 33/105
See application file for complete search history.

(56) References Cited

FOREIGN PATENT DOCUMENTS

| CN | 1857704 A | 11/2006 |
|---|---|---|
| KR | 10-0543862 B1 | 1/2006 |

(Continued)

OTHER PUBLICATIONS

Saba, "Black ginseng extract ameliorates hypercholesterolemia in rats", J. Ginseng Res, 2016, (40), pp. 160-168 (Year: 2016).*

(Continued)

*Primary Examiner* — Changqing Li
(74) *Attorney, Agent, or Firm* — The PL Law Group, PLLC

(57) ABSTRACT

A method for producing black *ginseng* concentrate is characterized by including steps of adding red *ginseng* to a continuous steaming-dryer followed by steaming, cooling, and drying to prepare black *ginseng*, carrying out extraction by adding alcohol to crushed black *ginseng* obtained by crushing the black *ginseng* prepared above followed by filtration to prepare black *ginseng* extract, and concentrating the black *ginseng* extract prepared above by using a plate type evaporative concentrator followed by heat treatment, and the present invention also relates to black *ginseng* concentrate prepared by the aforementioned method.

6 Claims, 7 Drawing Sheets

(51) Int. Cl.
  *A23L 19/10*  (2016.01)
  *A23L 33/105* (2016.01)
  *B01D 1/00*   (2006.01)

(56) References Cited

FOREIGN PATENT DOCUMENTS

| KR | 10-0753771 B1 | 8/2007 |
|---|---|---|
| KR | 10-2003528 B1 | 7/2019 |
| KR | 10-2020-0145254 A | 12/2020 |
| KR | 10-2297181 B1 | 9/2021 |
| KR | 10-2346875 B1 | 1/2022 |
| WO | WO 2007/061162 A1 | 5/2007 |

OTHER PUBLICATIONS

European Search Report For EP22186905.0 issued on Jan. 3, 2023 from European patent office in a counterpart European patent application.

Kwon, Myo Jin et al., "Optimal Conditions for Extracting the Ginsenosides Rg3, Rg5,and Rk1 from BlackGinseng", Journal of Food and Nutrition Research, vol. 5(3), pp. 176-179, 2017.

Metwaly Ahmed M. et al., "Black Ginseng and Its Saponis, Prepation, Phytochemistry and Pharmacological Effects", Molecules, vol. 24(10), p. 1856, 2019.

\* cited by examiner

METHOD FOR PRODUCING BLACK GINSENG CONCENTRATE WITH INCREASED PROSAPOGENIN GINSENOSIDE CONTENT USING CONTINUOUS STEAMING-DRYING TECHNIQUE AND COMBINED CONCENTRATION TECHNOLOGY

CROSS REFERENCE TO RELATED APPLICATIONS AND CLAIM OF PRIORITY

This application claims priority from Korean Patent Application No. 10-2022-0017912 filed on Feb. 11, 2022, in the Korean Intellectual Property Office, and all the benefits accruing therefrom under 35 U.S.C. 119, the contents of which in its entirety are herein incorporated by reference.

BACKGROUND

1. Technical Field

The present invention relates to a method for producing black *ginseng* concentrate characterized by including steps of: (1) steaming *ginseng* followed by drying to prepare red *ginseng*; (2) carrying out extraction by adding water to a black *ginseng* mixture containing black *ginseng*, *Patrinia scabiosaefolia* roots, *Persicaria hydropiper* (i.e., water pepper) leaves, and *Persicaria thunbergii* leaves followed by filtration to prepare a mixed plant extract; (3) having the red *ginseng*, which is prepared in the step (1), immersed in the mixed plant extract prepared in the step (2) followed by recovery from the extract; (4) placing the red *ginseng* recovered in the step (3) in a continuous steaming dryer followed by steaming, cooling, and drying to prepare black *ginseng*; (5) carrying out extraction of crushed black *ginseng*, which is obtained by crushing the black *ginseng* prepared in the step (4), by adding alcohol followed by filtration to prepare a black *ginseng* extract, and (6) concentrating the black *ginseng* extract prepared in the step (5) by using a plate type evaporative concentrator followed by heat treatment. The present invention also relates to black *ginseng* concentrate prepared by the aforementioned method.

2. Background Art

Ginsenoside is a saponin compound present in *ginseng*. Being recently known to have anti-cancer, anti-oxidation, and cholesterol-reducing effects, it comes into the spotlight as a promising physiologically active material. Unlike the saponins found in other plants, *ginseng* saponin has a characteristic structure and also special pharmacological efficacy. *Ginseng* saponin is called "ginsenoside", meaning "*ginseng* glycoside".

The component specifically found in red *ginseng* is an artificial product in prosapogenin form, which is produced by thermal hydrolysis of *ginseng* saponin glycoside. As a prosapogenin component generated during the production of red *ginseng*, ginsenoside Rg5, Rg6, Rk1, Rk3, Rh4, F1, F4 and the like currently attract considerable attention.

While red *ginseng* is steamed and dried only once, black *ginseng* requires steaming and drying at least three times (in particular, black *ginseng* obtained by steaming and drying, each nine times, is called nine-steamed and nine-dried black *ginseng*). During the process of producing black *ginseng*, not only a color change, i.e., white (un-dried raw *ginseng*, white *ginseng*)→reddish brown (red *ginseng*)→blackish brown (black *ginseng*), but also a change in taste and usefulness is caused. Examples of the *ginseng* prosapogenin component produced during the production of black *ginseng* include ginsenoside Rg2, Rg3, Rg5, Rg6, Rk1, Rk3, Rh1, Rh2, Rh4, F1, and F4.

In Korean Patent Registration No. 0753771, a method for producing black *ginseng* and black *ginseng* concentrate is disclosed and, in Korean Patent Registration No. 0543862, black *ginseng* and black *ginseng* concentrate with high content of active components are disclosed. However, they are different from the method for producing black *ginseng* concentrate with increased prosapogenin ginsenoside content of the present invention.

SUMMARY

The present invention is devised under the circumstances described in the above, and object of the present invention is to provide a method for producing black *ginseng* concentrate having increased content of prosapogenin ginsenosides, which are specifically found in black *ginseng*, and also high production efficiency, high quality, and high preference achieved by efficient steaming-drying and concentration.

To solve the problems described in the above, the present invention provides a method for producing black *ginseng* concentrate characterized by including steps of: (1) steaming *ginseng* followed by drying to prepare red *ginseng*; (2) carrying out extraction by adding water to a black *ginseng* mixture containing black *ginseng*, *Patrinia scabiosaefolia* roots, *Persicaria hydropiper* leaves, and *Persicaria thunbergii* leaves followed by filtration to prepare a mixed plant extract; (3) having the red *ginseng*, which is prepared in the step (1), immersed in the mixed plant extract prepared in the step (2) followed by recovery from the extract; (4) placing the red *ginseng* recovered in the step (3) in a continuous steaming dryer followed by steaming, cooling, and drying to prepare black *ginseng*; (5) carrying out extraction of crushed black *ginseng*, which is obtained by crushing the black *ginseng* prepared in the step (4), by adding alcohol followed by filtration to prepare a black *ginseng* extract, and (6) concentrating the black *ginseng* extract prepared in the step (5) by using a plate type evaporative concentrator followed by heat treatment.

The present invention also provides black *ginseng* concentrate prepared by the aforementioned method.

By keeping the loss of effective components at minimum level during the production process, the black *ginseng* concentrate of the present invention can be produced more efficiently and can have higher content of specific ginsenosides. It is also advantageous in that the black *ginseng* concentrate has excellent flavor and high preference.

DETAILED DESCRIPTION

Figure 1:
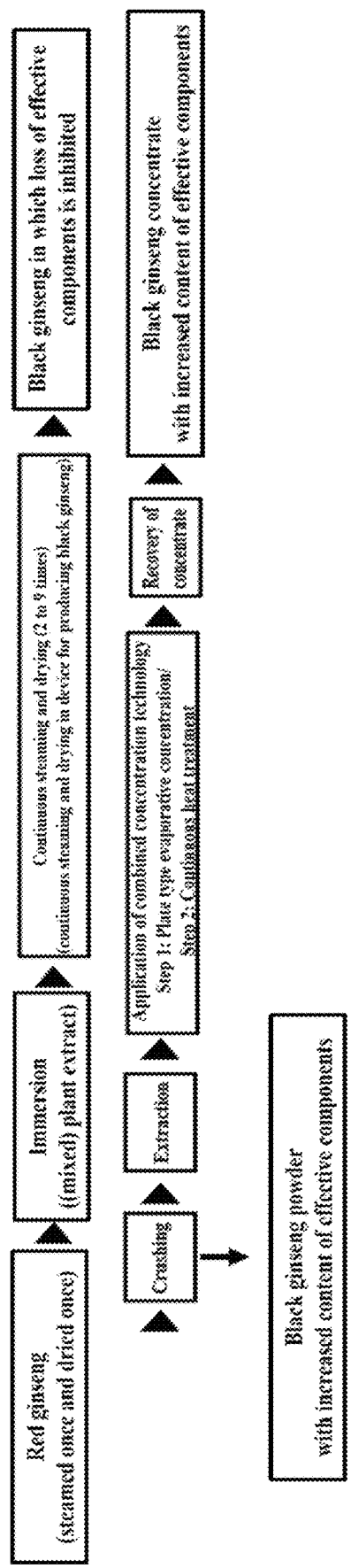
FIG. 1 is a diagram schematically illustrating the process for producing black *ginseng* concentrate of the present invention.

To achieve the object of the present invention, the present invention provides a method for producing black *ginseng* concentrate characterized by including steps of:

(1) steaming *ginseng* followed by drying to prepare red *ginseng*;

(2) carrying out extraction by adding water to a black *ginseng* mixture containing black *ginseng*, *Patrinia scabiosaefolia* roots, *Persicaria hydropiper* leaves, and *Persicaria thunbergii* leaves followed by filtration to prepare a mixed plant extract;

(3) having the red *ginseng*, which is prepared in the step (1), immersed in the mixed plant extract prepared in the step (2) followed by recovery from the extract;

(4) placing the red *ginseng* recovered in the step (3) in a continuous steaming dryer followed by steaming, cooling, and drying to prepare black *ginseng*;

(5) carrying out extraction of crushed black *ginseng*, which is obtained by crushing the black *ginseng* prepared in the step (4), by adding alcohol followed by filtration to prepare a black *ginseng* extract, and (6) concentrating the black *ginseng* extract prepared in the step (5) by using a plate type evaporative concentrator followed by heat treatment.

With regard to the method for producing black *ginseng* concentrate according to the present invention, the red *ginseng* of the step (1) may be preferably prepared by steaming *ginseng* for 1 to 3 hours at 90 to 110° C. followed by drying such that the *ginseng* has moisture content of not more than 12 to 18% (v/w) at 45 to 55° C. More preferably, it may be prepared by steaming *ginseng* for 2 hours at 100° C. followed by drying such that the *ginseng* has moisture content of not more than 15% (v/w) at 50° C. to give red *ginseng* that is suitable for producing black *ginseng*.

Furthermore, with regard to the method for producing black *ginseng* concentrate according to the present invention, the mixed plant extract of the step (2) may be preferably prepared by carrying out extraction for 1 to 3 hours at 80 to 90° C. by adding water in an amount of 7 to 9 times (v/w) the black *ginseng* mixture containing, based on the total weight of black *ginseng* mixture, 48 to 52% by weight of black *ginseng*, 18 to 22% by weight of *Patrinia scabiosaefolia* roots, 18 to 22% by weight of *Persicaria hydropiper* leaves, and 8 to 12% by weight of *Persicaria thunbergii* leaves followed by filtration. More preferably, it may be prepared by carrying out extraction for 2 hours at 85° C. by adding water in an amount of 8 times (v/w) the black *ginseng* mixture containing, based on the total weight of black *ginseng* mixture, 50% by weight of black *ginseng*, 20% by weight of *Patrinia scabiosaefolia* roots, 20% by weight of *Persicaria hydropiper* leaves, and 10% by weight of *Persicaria thunbergii* leaves followed by filtration. When red *ginseng* is immersed using the mixed plant extract prepared as described above, ginsenoside content in red *ginseng* can be increased more while the dissolution of the effective components of red *ginseng* is kept at minimum level, and the pre-treatment with mild red *ginseng* having excellent preference can be also achieved.

Furthermore, with regard to the method for producing black *ginseng* concentrate according to the present invention, the step (3) may preferably have the red *ginseng* immersed for 2 to 4 hours at 45 to 55° C. in the mixed plant extract followed by recovery from the extract. More preferably, the step (3) may have the red *ginseng* immersed for 3 hours at 50° C. in the mixed plant extract followed by recovery from the extract. By carrying out the immersion at the aforementioned conditions, more efficient immersion can be achieved and also content of specific ginsenosides can be increased more.

Furthermore, with regard to the method for producing black *ginseng* concentrate according to the present invention, the black *ginseng* of the step (4) may be preferably prepared by, after placing the red *ginseng* in a continuous steaming dryer, repeating 7 to 9 times the following process of steaming, cooling, and drying including steaming the red *ginseng* for 4 to 8 hours at temperature of 90 to 95° C. and humidity of 90 to 95% after treating it for 60 to 90 minutes at temperature of 50 to 55° C. and humidity of 90 to 95%; cooling for 60 to 90 minutes at humidity of 90 to 95% to temperature of 25 to 30° C. after lowering the temperature for 60 to 90 minutes at humidity of 90 to 95% to temperature of to 55° C.; and drying at 50 to 55° C. while no moisture is supplied to the continuous steaming dryer. More preferably, the black *ginseng* of the step (4) may be prepared by repeating 8 times the above process of steaming, cooling, and drying.

According to a common process for producing black *ginseng*, the steaming is carried out with a steamer in which moisture is present during the steaming and drying, and the drying is carried out after transfer to a dryer. However, in the present invention, steaming-drying and drying are carried out by using a continuous steaming dryer which allows supply and discharge of moisture and temperature increase, and thus more efficient steaming and drying of *ginseng* can be achieved. In addition, since the yield is high and loss of the effective components is kept at minimum level during the production process, higher content of specific ginsenosides in final black *ginseng* can be also obtained.

Furthermore, with regard to the method for producing black *ginseng* concentrate according to the present invention, the black *ginseng* extract of the step (5) may be prepared by carrying out extraction for 1 to 3 hours at 55 to 60° C. of crushed black *ginseng*, which is obtained by crushing the black *ginseng*, by adding 60 to 80% (v/v) alcohol in an amount of 7 to 9 times (v/w) the crushed black *ginseng* followed by filtration. More preferably, it may be prepared by carrying out extraction for 2 hours at 55 to 60° C. of crushed black *ginseng*, which is obtained by crushing the black *ginseng*, by adding 70% (v/v) alcohol in an amount of 8 times (v/w) the crushed black *ginseng* followed by filtration so that the effective components in black *ginseng* can be extracted at maximum level.

Still furthermore, with regard to the method for producing black *ginseng* concentrate according to the present invention, the step (6) may be preferably concentrating the black *ginseng* extract at 50 to 60° C. by using a plate type evaporative concentrator till to have Brix value of 67 to 71 followed by heat treatment for 5 to 7 hours at 85 to 95° C. More preferably, it may be concentrating the black *ginseng* extract at 55° C. by using a plate type evaporative concentrator till to have Brix value of 69 followed by heat treatment for 6 hours at 85 to 95° C. When the black *ginseng* extract is heat-treated after concentration at the above conditions, content of specific ginsenosides can be increased and also more efficient concentration can be achieved.

More specifically, the method for producing black *ginseng* concentrate according to the present invention may include steps of:
(1) steaming *ginseng* for 1 to 3 hours at 90 to 110° C. followed by drying such that it has moisture content of not more than 12 to 18% (v/w) at 45 to 55° C. to prepare red *ginseng*;
(2) carrying out extraction for 1 to 3 hours at 80 to 90° C. by adding water in an amount of 7 to 9 times (v/w) a black *ginseng* mixture containing, based on the total weight of black *ginseng* mixture, 48 to 52% by weight of black *ginseng*, 18 to 22% by weight of *Patrinia scabiosaefolia* roots, 18 to 22% by weight of *Persicaria hydropiper* leaves, and 8 to 12% by weight of *Persicaria thunbergii* leaves followed by filtration to prepare a mixed plant extract;
(3) having the red *ginseng*, which is prepared in the step (1), immersed for 2 to 4 hours at 45 to 55° C. in the mixed plant extract prepared in the step (2) followed by recovery from the extract;
(4) placing the red *ginseng* recovered in the step (3) in a continuous steaming dryer followed by repeating 7 to 9 times a process of steaming, cooling, and drying to prepare black *ginseng*;
(5) carrying out extraction for 1 to 3 hours at 55 to 60° C. of crushed black *ginseng*, which is obtained by crushing the black *ginseng* prepared in the step (4), by adding 60 to 80% (v/v) alcohol in an amount of 7 to 9 times (v/w) the crushed black *ginseng* followed by filtration to prepare a black *ginseng* extract, and
(6) concentrating at 50 to 60° C. the black *ginseng* extract prepared in the step (5) by using a plate type evaporative concentrator till to have Brix value of 67 to 71 followed by heat treatment for 5 to 7 hours at 85 to 95° C.

Even more specifically, the method may include steps of:
(1) steaming *ginseng* for 2 hours at 100° C. followed by drying such that it has moisture content of not more than 15% (v/w) at 50° C. to prepare red *ginseng*;
(2) carrying out extraction for 2 hours at 85° C. by adding water in an amount of 8 times (v/w) a black *ginseng* mixture containing, based on the total weight of black *ginseng* mixture, 50% by weight of black *ginseng*, 20% by weight of *Patrinia scabiosaefolia* roots, 20% by weight of *Persicaria hydropiper* leaves, and 10% by weight of *Persicaria thunbergii* leaves followed by filtration to prepare a mixed plant extract;
(3) having the red *ginseng*, which is prepared in the step (1), immersed for 3 hours at 50° C. in the mixed plant extract prepared in the step (2) followed by recovery from the extract;
(4) placing the red *ginseng* recovered in the step (3) in a continuous steaming dryer followed by repeating 8 times a process of steaming, cooling, and drying to prepare black *ginseng*;
(5) carrying out extraction for 2 hours at 55 to 60° C. of crushed black *ginseng*, which is obtained by crushing the black *ginseng* prepared in the step (4), by adding 70% (v/v) alcohol in an amount of 8 times (v/w) the crushed black *ginseng* followed by filtration to prepare a black *ginseng* extract, and
(6) concentrating at 55° C. the black *ginseng* extract prepared in the step (5) by using a plate type evaporative concentrator till to have Brix value of 69 followed by heat treatment for 6 hours at 85 to 95° C.

The present invention also provides black *ginseng* concentrate prepared by the aforementioned method.

The black *ginseng* concentrate of the present invention is characterized in that it has increased content of prosapogenin ginsenosides that are produced during the production of black *ginseng*. The prosapogenin ginsenosides may be one or more ginsenosides selected from the group consisting of Rk1, Rg5, and Rg3, but not limited thereto.

Hereinbelow, the present invention is explained in greater detail in view of the Preparation examples and Examples. However, the following Preparation examples and Examples are given only for exemplification of the present invention, and it would be evident to a person who has common knowledge in the pertinent art that the scope of the present invention is not limited by them.

EXAMPLES

Preparation Example 1. Black *Ginseng* Concentrate (Extract Immersion—Continuous Steaming-Drying—Plate Type Evaporative Concentration—Heat Treatment)

(1) *Ginseng* was steamed once for 2 hours at 100° C., and then dried at 50° C. to have moisture content of not more than 15% to prepare red *ginseng*.
(2) Extraction was carried out for 2 hours at 85° C. by adding purified water in an amount of 8 times (v/w) the black *ginseng* mixture containing, based on the total weight of black *ginseng* mixture, 50% by weight of black *ginseng*, 20% by weight of *Patrinia scabiosaefolia* (*Dahurian patrinia*) roots, 20% by weight of *Persicaria hydropiper* leaves, and 10% by weight of*Persicaria thunbergii* leaves followed by filtration to prepare a mixed plant extract.
(3) Red *ginseng* prepared in the step (1) was immersed for 3 hours at 50° C. in the mixed plant extract prepared in the step (2), and then removed from the extract.
(4) Red *ginseng* recovered in the step (3) was placed in a continuous steaming dryer, and then the process of steaming, cooling, and drying was repeated 8 times to prepare black *ginseng*. With regard to the steaming, cooling, and drying, the process of steaming, cooling, and drying including the following was repeated 8 times to prepare black *ginseng*: steaming the red *ginseng* for 4 to 8 hours at temperature of 90 to 95° C. and humidity of 90 to 95% after placing the immersed red *ginseng* in a continuous steaming dryer for preparing black *ginseng*, which has been preheated for 30 to 60 minutes at temperature of 50 to 55° C. and humidity of 90 to 95% (the reactor is supplied with moisture), and treating the *ginseng* for 60 to 90 minutes at temperature of 50 to 55° C. and humidity of 90 to 95% while maintaining atmospheric pressure; cooling for 60 to 90 minutes at humidity of 90 to 95% to temperature of 25 to 30° C. after lowering the temperature for 60 to 90 minutes at humidity of 90 to 95% to temperature of 45 to 55° C.; and drying at 50 to 55° C. while no moisture is supplied to the continuous steaming dryer for preparing black *ginseng*. The drying was carried out for 5 to 9 hours for the $1^{st}$ drying to $7^{th}$ drying, but for 36 to 72 hours for the 8th drying so that the moisture content in the final black *ginseng* is not more than 16%.
(5) Crushed black *ginseng*, which has been obtained by crushing the black *ginseng* prepared in the step (4), was extracted for 2 hours at 55 to 60° C. by adding 70% (v/v) alcohol in an amount of 8 times (v/w) the crushed black *ginseng*, and then filtered to prepare a black *ginseng* extract.

(6) Black *ginseng* extract prepared in the step (5) was concentrated at 55° C. by using a plate type evaporative concentrator till to have Brix value of 69, and then subjected to heat treatment for 6 hours at 85 to 95° C. (FIG. 1).

Comparative Example 1. Black *Ginseng* Concentrate (Water Immersion—General Steaming-Drying—Concentration Under Reduced Pressure)

(1) *Ginseng* was steamed once for 2 hours at 100° C., and then dried at 50° C. to have moisture content of not more than 15% to prepare red *ginseng*.
(2) Red *ginseng* prepared in the step (1) was immersed for 3 hours at 50° C. in purified water, and then removed from the water.
(3) Purified water was added to a steamer container, the red *ginseng* recovered in the step (2) was placed on a steamer tray, and then the process of steaming, cooling, and drying was repeated 8 times to prepare black *ginseng*, in which the process of steaming, cooling, and drying includes steaming the red *ginseng* for 4 to 8 hours at temperature of 100° C.; turning off the steamer and lowering the temperature to 25 to 30° C.; and transferring the *ginseng* to hot air dryer and drying it at 50 to 55° C. The drying was carried out for 5 to 9 hours for the $1^{st}$ drying to $7^{th}$ drying, but for 36 to 72 hours for the $8^{th}$ drying so that the moisture content in the final black *ginseng* is not more than 16%.
(4) Crushed black *ginseng*, which has been obtained by crushing the black *ginseng* prepared in the step (3), was extracted for 2 hours at 55 to 60° C. by adding 70% (v/v) alcohol in an amount of 8 times (v/w) the crushed black *ginseng*, and then filtered to prepare a black *ginseng* extract.
(5) Black *ginseng* extract prepared in the step (4) was concentrated at 65 to 70° C. by using a reduced pressure concentrator till to have Brix value of 69.

Comparative Example 2. Black *Ginseng* Concentrate (Continuous Steaming-Drying—Plate Type Evaporative Concentration—Heat Treatment)

(1) *Ginseng* was steamed once for 2 hours at 100° C., and then dried at 50° C. to have moisture content of not more than 15% to prepare red *ginseng*.
(2) Red *ginseng* prepared in the step (1) was immersed for 3 hours at 50° C. in purified water, and then removed from the water.
(3) By using the red *ginseng* removed in the step (2), black *ginseng* concentrate was prepared in the same manner as the step (4) to step (6) of Preparation example 1.

Comparative Example 3. Black *Ginseng* Concentrate (Extract Immersion—General Steaming-Drying—Plate Type Evaporative Concentration—Heat Treatment)

(1) *Ginseng* was steamed once for 2 hours at 100° C., and then dried at 50° C. to have moisture content of not more than 15% to prepare red *ginseng*.
(2) Extraction was carried out for 2 hours at 85° C. by adding purified water in an amount of 8 times (v/w) the black *ginseng* mixture containing, based on the total weight of black *ginseng* mixture, 50% by weight of black *ginseng*, 20% by weight of *Patrinia scabiosaefolia* (*Dahurian patrinia*) roots, 20% by weight of *Persicaria hydropiper* leaves, and 10% by weight of *Persicaria thunbergii* leaves followed by filtration to prepare a mixed plant extract.
(3) Red *ginseng* prepared in the step (1) was immersed for 3 hours at 50° C. in the mixed plant extract prepared in the step (2), and then removed from the extract.
(4) Purified water was added to a steamer container, red *ginseng* recovered in the step (3) was placed on a steamer tray, and then the process of steaming, cooling, and drying was repeated 8 times to prepare black *ginseng*, in which the process of steaming, cooling, and drying includes steaming the red *ginseng* for 4 to 8 hours at temperature of 100° C.; turning off the steamer and lowering the temperature to 25 to 30° C.; and transferring the *ginseng* to hot air dryer and drying it at 50 to 55° C. The drying was carried out for 5 to 9 hours for the $1^{st}$ drying to $7^{th}$ drying, but for 36 to 72 hours for the 8th drying so that the moisture content in the final black *ginseng* is not more than 16%.
(5) Crushed black *ginseng*, which has been obtained by crushing the black *ginseng* prepared in the step (4), was extracted for 2 hours at 55 to 60° C. by adding 70% (v/v) alcohol in an amount of 8 times (v/w) the crushed black *ginseng*, and then filtered to prepare a black *ginseng* extract.
(6) Black *ginseng* extract prepared in the step (5) was concentrated at 55° C. by using a plate type evaporative concentrator till to have Brix value of 69, and then subjected to heat treatment for 6 hours at 85 to 95° C.

Comparative Example 4. Black *Ginseng* Concentrate (Extract Immersion—Continuous Steaming-Drying—Concentration Under Reduced Pressure—Heat Treatment)

(1) Black *ginseng* extract was prepared in the same manner as the step (1) to step (5) of Preparation example 1.
(2) Black *ginseng* extract prepared in the step (1) was concentrated at 65 to 70° C. by using a reduced pressure concentrator till to have Brix value of 69, and then subjected to heat treatment for 6 hours at 85 to 95° C.

1. Preparation of Black *Ginseng* Concentrate
(1) Red *Ginseng* Preparation
*Ginseng* was steamed once for 2 hours at 100° C., and then dried at 50° C. to have moisture content of not more than 15%. Red *ginseng* was obtained accordingly.
(2) Immersion
Red *ginseng* prepared in the above was immersed for 3 hours at 50° C. in a mixed plant extract, and then removed from the extract.
(3) Continuous Steaming-Drying
Schematic diagram of the continuous steaming dryer for preparing black *ginseng*, which has been used for continuous steaming-drying of red *ginseng* of the present invention, is given in FIG. 2. Steaming and drying of *ginseng* occur on a tray that is present inside the reaction part, and there is a control board of a control part, which controls not only the temperature and humidity inside the reaction part but also the reaction time.

Red *ginseng* removed after immersion as described above was arranged on a tray inside the reaction part of a continuous steaming dryer for preparing black *ginseng*, and, by repeating 8 times the process of steaming, cooling, and drying at the conditions described in the following Table 1, black *ginseng* was prepared. By supplying moisture from the reservoir tank containing water to the reaction part of a continuous steaming dryer for preparing black *ginseng*, high humidity was maintained, and temperature of the reaction part was raised by applying electric heat to carry out the *ginseng* steaming. To maintain the internal pressure at atmospheric pressure during the streaming, vapor was allowed to get discharged via the vapor discharge line.

Figure 2:
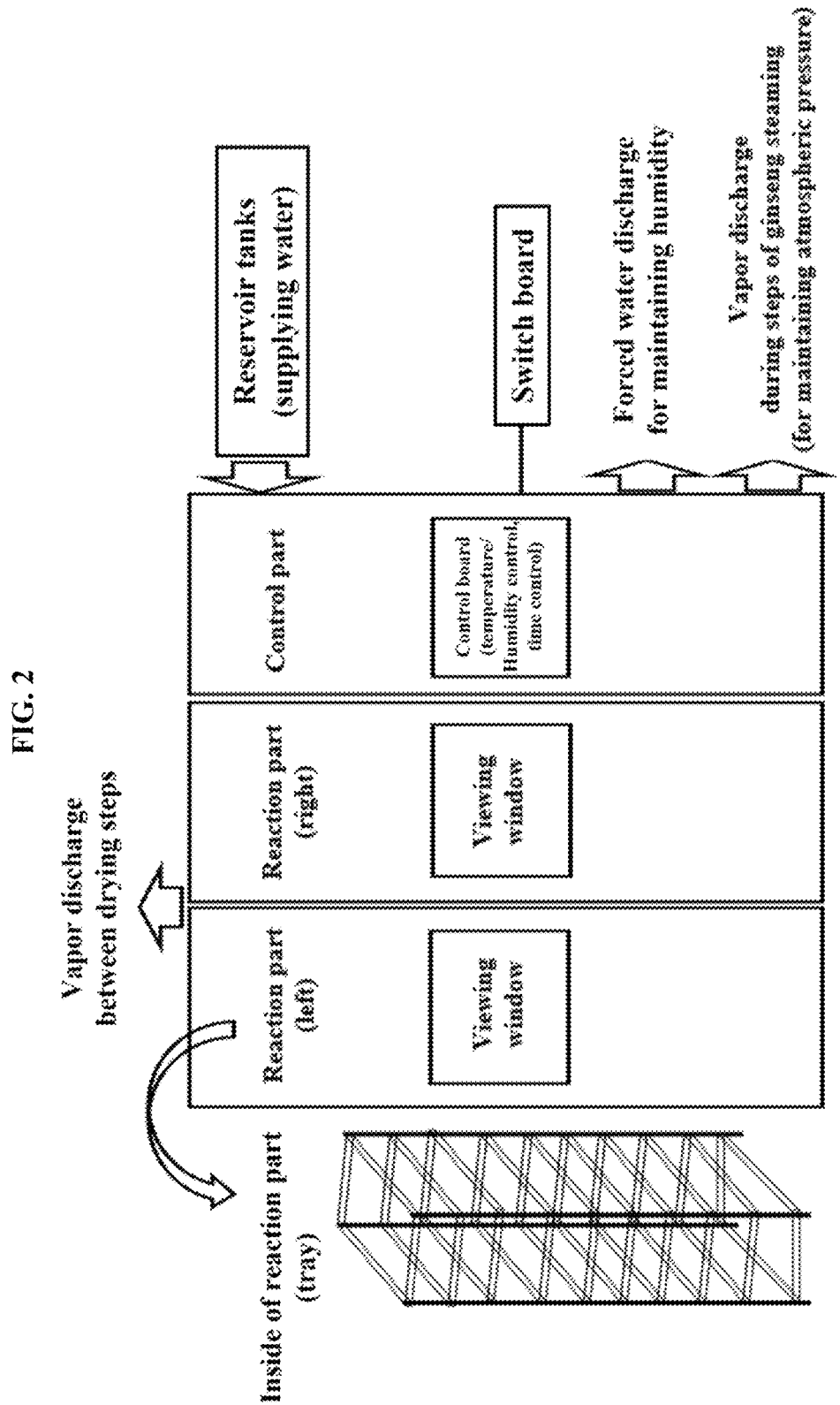
FIG. 2 is a brief diagram of a continuous steaming dryer for preparing black *ginseng* which has been used for steaming, cooling, and drying to produce the black *ginseng* of the present invention.
Figure 3:
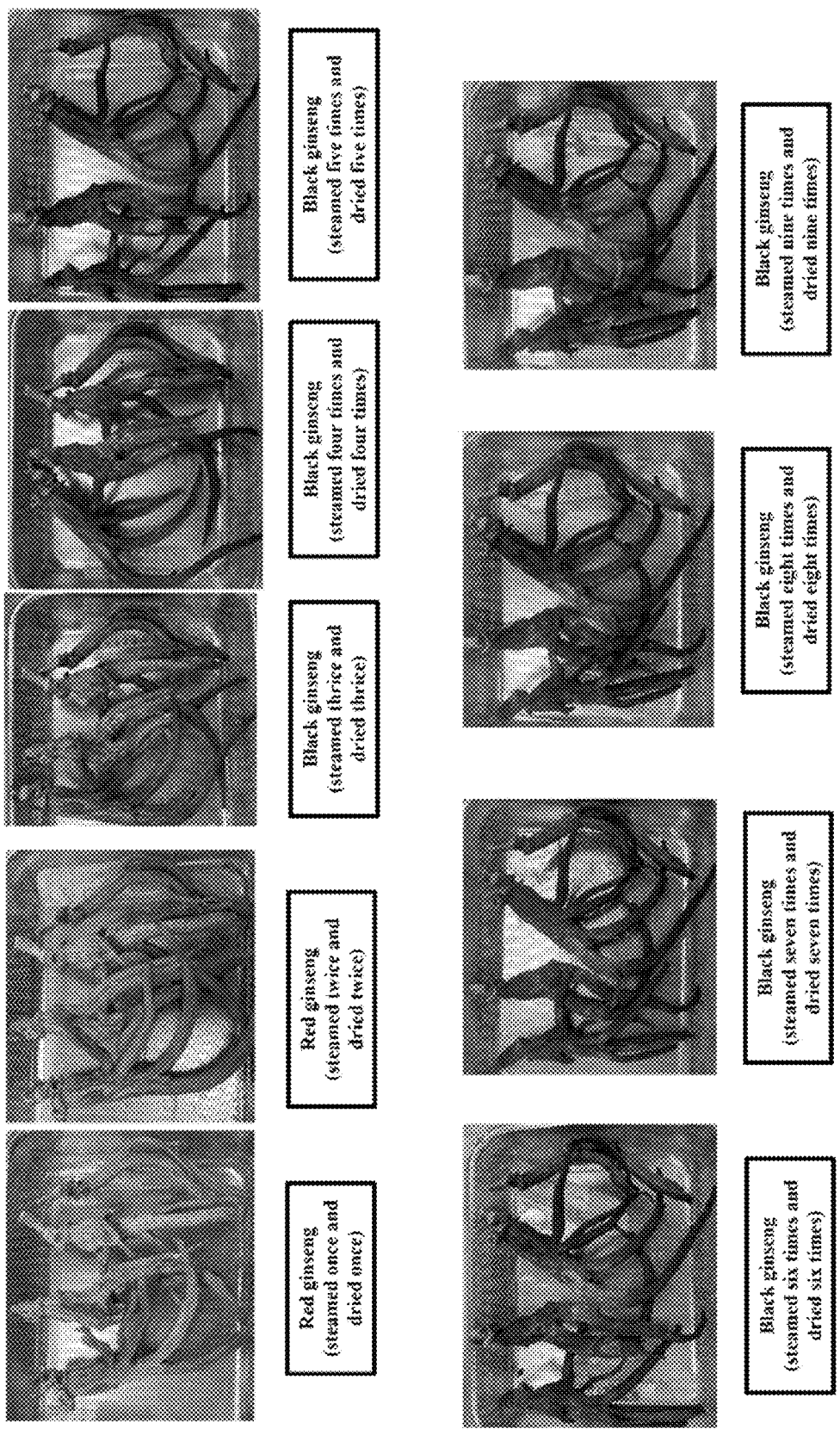
FIG. 3 is a photographic image for comparing the outer appearance between red *ginseng* and black *ginseng*, depending on the number of steaming-drying of the present invention.

Furthermore, after discharging the vapor present in the reaction part of a continuous steaming dryer for preparing black *ginseng* during drying, the reaction part was heated with electric heat to carry out drying. For the last drying, drying was carried out for 36 to 72 hours so that the moisture content in the final black *ginseng* is not more than 16% (FIGS. 2 and 3).

TABLE 1

Operation conditions of continuous steaming dryer for preparing black ginseng

| Step | Remarks | Temperature (° C.) | Humidity (%) | Time (hr) |
|---|---|---|---|---|
| Pre-heating step | | 50 to 55 | 90 to 95 | 0.5 to 1 |
| Steaming step | 1 to 8 times | 50 to 55 | 90 to 95 | 1 to 1.5 |
| | | 90 to 95 | 90 to 95 | 4 to 8 |
| Cooling step | 1 to 8 times | 45 to 55 | 90 to 95 | 1 to 1.5 |
| | | 25 to 30 | 90 to 95 | 1 to 1.5 |
| Drying step | 1 to 7 times | 50 to 55 | x | 5 to 9 |
| | 8 times | 50 to 55 | x | 36 to 72 |

(4) Alcohol Extraction

Crushed black *ginseng*, which has been obtained as described in the above, was extracted for 2 hours at 55 to 60° C. by adding 70% (v/v) alcohol in an amount of 8 times (v/w) the crushed black *ginseng*, and then filtered to prepare a black *ginseng* extract.

(5) Combined Concentration Technology

Figure 4:
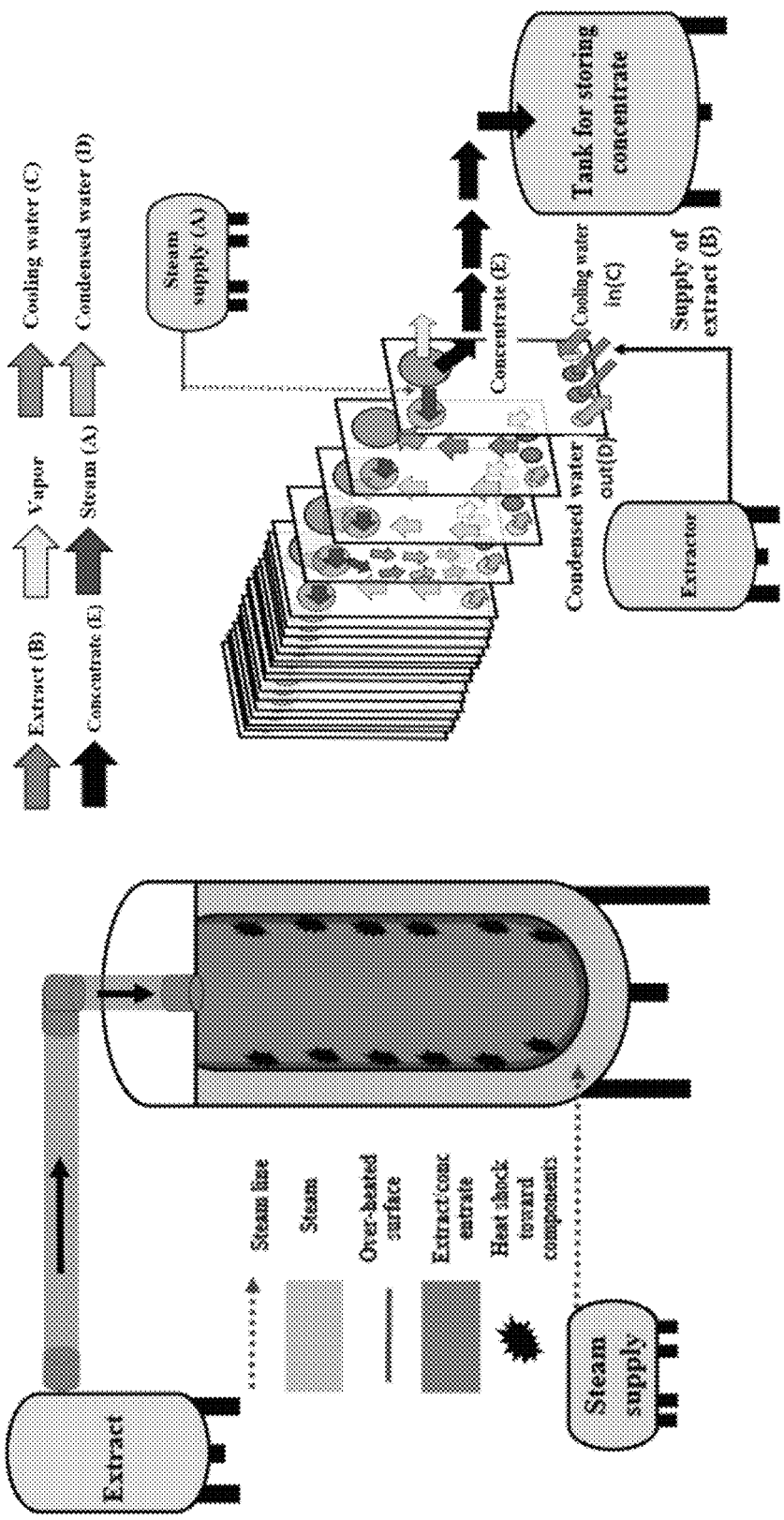
FIG. 4 is a brief diagram for comparing the basic principle for concentrating the black *ginseng* extract between reduced pressure concentrator and plate type evaporative concentrator.

According to the reduced-pressure concentration using reduced pressure concentrator which is generally used, steam is supplied to the inside of a double jacket of tank during the concentration step. In this regard, there is a possibility of having continuous breakage of components caused by momentary heat shock on jacket contact area, which occurs during the evaporation process of liquid extract (FIG. 4).

The plate type evaporative concentrator (i.e., plate evaporator) used in the present invention is also referred to as 'plate type heating concentrator', 'plate concentrator', or "plate evaporative concentration system', and it allows only minimum thermal damage of liquid extract by overcoming the problems of reduced-pressure concentration as described in the above. In addition, by having a mode of allowing the heating, cooling, evaporation, and condensation to occur within a space formed between plural plates, it is advantageous in that it has better efficiency than reduced-pressure concentration.

When the black *ginseng* extract prepared as described in the above is supplied to the lower part of the plate type evaporative concentrator, in which plural plates are stacked upon one another, water vapor is generated from the liquid extract due to the steam supplied from the upper part. The water vapor is then discharged as vapor, steam is condensed in accordance with supply of cooling water and consequently discharged in form of condensed water, and the liquid extract remained as vapor after discharge is obtained in concentrated form. Accordingly, black *ginseng* extract having final Brix value of 69 was recovered (FIG. 4 and Table 2).

Figure 5:
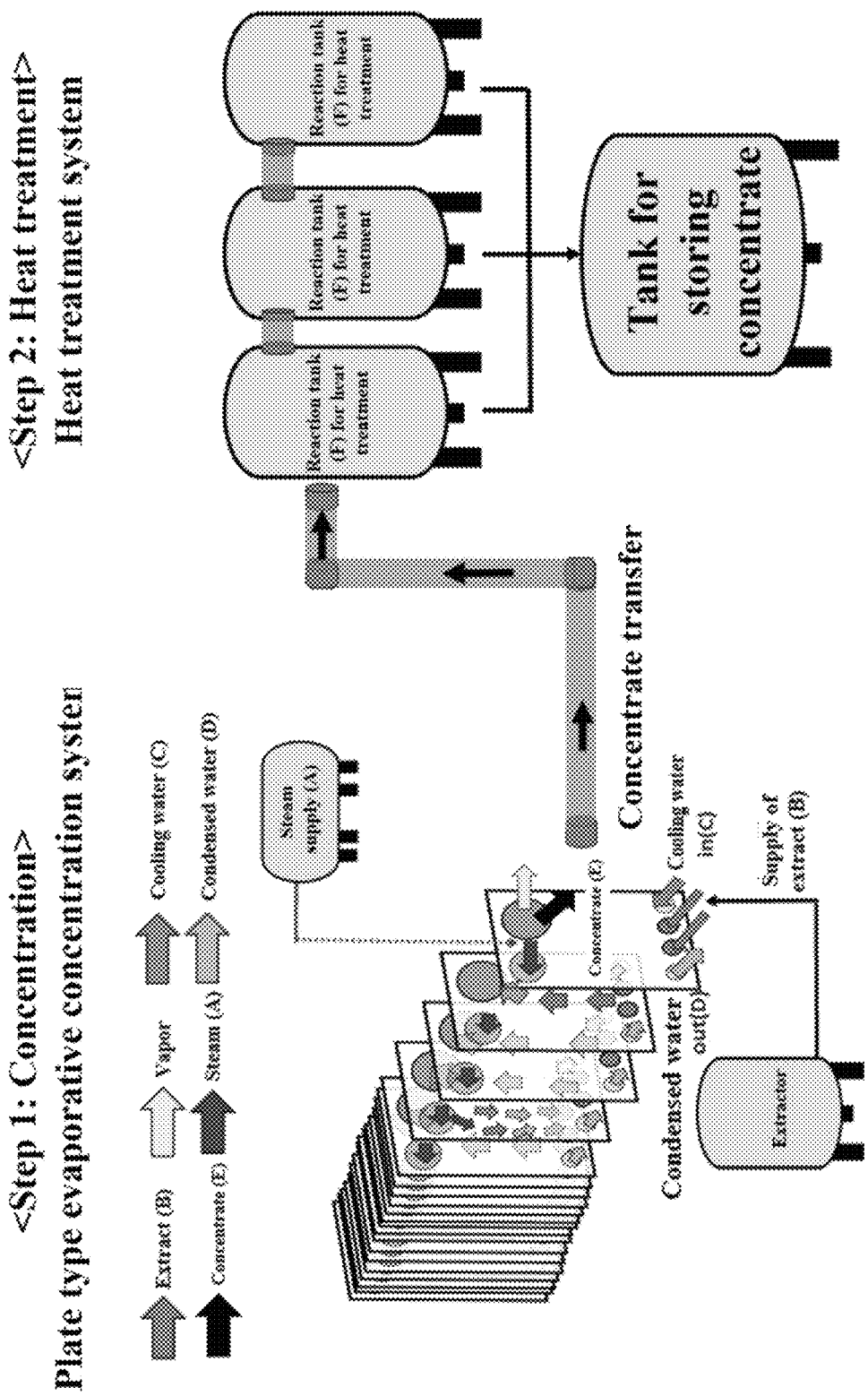
FIG. 5 is a brief diagram illustrating the process by the plate type evaporative concentrator for concentrating the black *ginseng* extract of the present invention, and the continuous heat treatment process.

The recovered black *ginseng* concentrate was transferred to a heat treatment system, and then subjected to a heat treatment at 85 to 95° C. for 6 hours (FIG. 5).

TABLE 2

Operation conditions of plate type evaporative concentrator

| Process | Flow rate | Concentration (Brix) | Temperature (° C.) | Pressure (bar) |
|---|---|---|---|---|
| Steam supply | 1,300 to 1,400 kg/h | — | — | 2.5 to 3.5 |
| Extract supply | 2,900 to 3,100 kg/h | 12 to 16 | 8 to 12 | 1.2 to 1.8 |
| Cooling water supply | 3 to 5 m³/h | — | 8 to 12 | 1.8 to 2.2 |
| Condensing water recovery | 3 to 5 m³/h | 15 to 18 | 15 to 18 | 1.3 to 1.7 |
| Concentrate recovery | 550 to 570 kg/h | 65 to 70 | 52 to 57 | 1.3 to 1.7 |

2. Method for Measuring Ginsenoside Content

Content of ginsenosides was analyzed by HPLC (High Performance Liquid Chromatography) equipped with UVD (Ultra Visible Detector), and the conditions for analysis are the same as those described in the following Table 3. Mathematical formula for calculating the content is given below.

Ginsenoside content (mg/g)=S×(a×b)/Collected sample amount (g)

S: Concentration of individual ginsenoside in test solution (mg/ml)

a: Total volume of test solution (ml)

b: Dilution fold

TABLE 3

Conditions for ginsenoside analysis

| Apparatus | HPLC Agilent 1260 series |
|---|---|
| Detector | DAD detector (203 nm) |
| Column | Prontosil 120-5-C18-ace-EPS (4.6 mm × 250 mm, 5.0 μm) |
| Column temperature | 40° C. |
| Mobile phase | Acetonitrile: D.W. (gradient) |
| Flow rate | 1.0 ml/min |
| Injection volume | 10 μl |

Example 1. Establishment of Conditions for Immersion in Mixed Plant Extract

Red *ginseng* was immersed in mixed plant extract. Then, moisture content and release level of red *ginseng* components at various immersion temperatures and various treatment times were analyzed.

As for the moisture content, it was not more than 50% even when the immersion was carried out for 6 hours at treatment temperature of 10° C. or 30° C. It was found that good immersion efficiency is obtained when the immersion is carried out at temperature of 50° C. or higher (Table 4).

TABLE 4

Variation in moisture content (%) in red ginseng

| Treatment temperature | Treatment time | Moisture content (%) in red ginseng after treatment |
|---|---|---|
| 10° C. | 1 Hour | 19.04 |
| | 2 Hours | 23.83 |
| | 3 Hours | 25.47 |
| | 6 Hours | 29.69 |
| 30° C. | 1 Hour | 16.46 |
| | 2 Hours | 26.04 |
| | 3 Hours | 30.83 |
| | 6 Hours | 42.28 |
| 50° C. | 1 Hour | 39.63 |
| | 2 Hours | 67.85 |
| | 3 Hours | 74.80 |
| | 6 Hours | 85.23 |
| 70° C. | 1 Hour | 16.57 |
| | 2 Hours | 61.60 |
| | 3 Hours | 80.44 |
| | 6 Hours | >90 |

Brix values, content of 3 kinds (i.e., total of Rb1, Rg1, and Rg3), and content of 3 kinds of black *ginseng* (i.e., total of Rk1, Rg5, and Rg3) are compared between the immersion solution and raw red *ginseng* after immersion at various immersion conditions, and the results are given in the following Table 5.

It was consequently found that, higher the immersion temperature and longer the immersion time are, more ginsenosides are released into the immersion solution. Moreover, since the 3 kinds of black *ginseng* ginsenoside of raw red *ginseng* after immersion is highest when the immersion is carried out for 3 hours at 50° C., it was decided that the immersion is to be performed at such conditions.

TABLE 5

Release level of red ginseng components

| | | | Immersion solution | | Raw red ginseng after immersion | |
|---|---|---|---|---|---|---|
| Analyte | | | | 3 Kinds | | 3 Kinds |
| Temperature | Time | Brix change | 3 Kinds (mg/g) | of black ginseng (mg/g) | 3 Kinds (mg/g) | of black ginseng (mg/g) |
| Control | | 10.26 | 1.203 | 1.513 | 4.52 | 0.19 |
| 10° C. | 1 Hour | 10.31 | 1.23 | 1.55 | 4.51 | 0.17 |
| | 2 Hours | 10.34 | 1.23 | 1.55 | 4.49 | 0.16 |
| | 3 Hours | 10.43 | 1.22 | 1.57 | 4.50 | 0.15 |
| | 6 Hours | 10.50 | 1.25 | 1.50 | 4.48 | 0.20 |
| 30° C. | 1 Hour | 10.33 | 1.24 | 1.56 | 4.53 | 0.22 |
| | 2 Hours | 10.62 | 1.25 | 1.57 | 4.54 | 0.24 |
| | 3 Hours | 10.87 | 1.27 | 1.59 | 4.50 | 0.23 |
| | 6 Hours | 10.90 | 1.30 | 1.57 | 4.55 | 0.21 |
| 50° C. | 1 Hour | 10.56 | 1.23 | 1.56 | 4.49 | 0.25 |
| | 2 Hours | 11.28 | 1.30 | 1.65 | 4.59 | 0.33 |
| | 3 Hours | 11.60 | 1.34 | 1.69 | 4.62 | 0.48 |
| | 6 Hours | 11.89 | 1.37 | 1.65 | 4.89 | 0.37 |
| 70° C. | 1 Hour | 10.44 | 1.39 | 1.75 | 4.57 | 0.27 |
| | 2 Hours | 11.84 | 1.36 | 1.74 | 4.68 | 0.37 |
| | 3 Hours | 13.19 | 1.43 | 1.8 | 4.59 | 0.39 |
| | 6 Hours | 13.83 | 1.47 | 2.03 | 4.51 | 0.25 |

Example 2. Effluent Analysis and Yield Depending on Number of Steaming

Ginsenoside content (sum of 1 to 8 times) obtained by using either a general steaming method in which *ginseng* is typically steamed with a steamer, or the method of the present invention in which *ginseng* is steamed under supply of moisture by using continuous steaming-dryer for preparing black *ginseng*, was analyzed, and the results are given in the following Table 6.

It was consequently found that, when the continuous steaming dryer for preparing black *ginseng* of the present invention is used, Rg1, Rb1 and Rg3 are detected from the effluent while Rg1 and Rb1 are detected from the general steaming.

TABLE 6

Ginsenoside content in effluent after ginseng steaming

| Group | Total of 3 kinds | Rg1 | Rb1 | Rg3 |
|---|---|---|---|---|
| Effluent after general steaming (mg/g) | 0.05 | 0.01 | 0.04 | ND |
| Effluent after continuous steaming (mg/g) | ND | ND | ND | ND |

Figure 6:
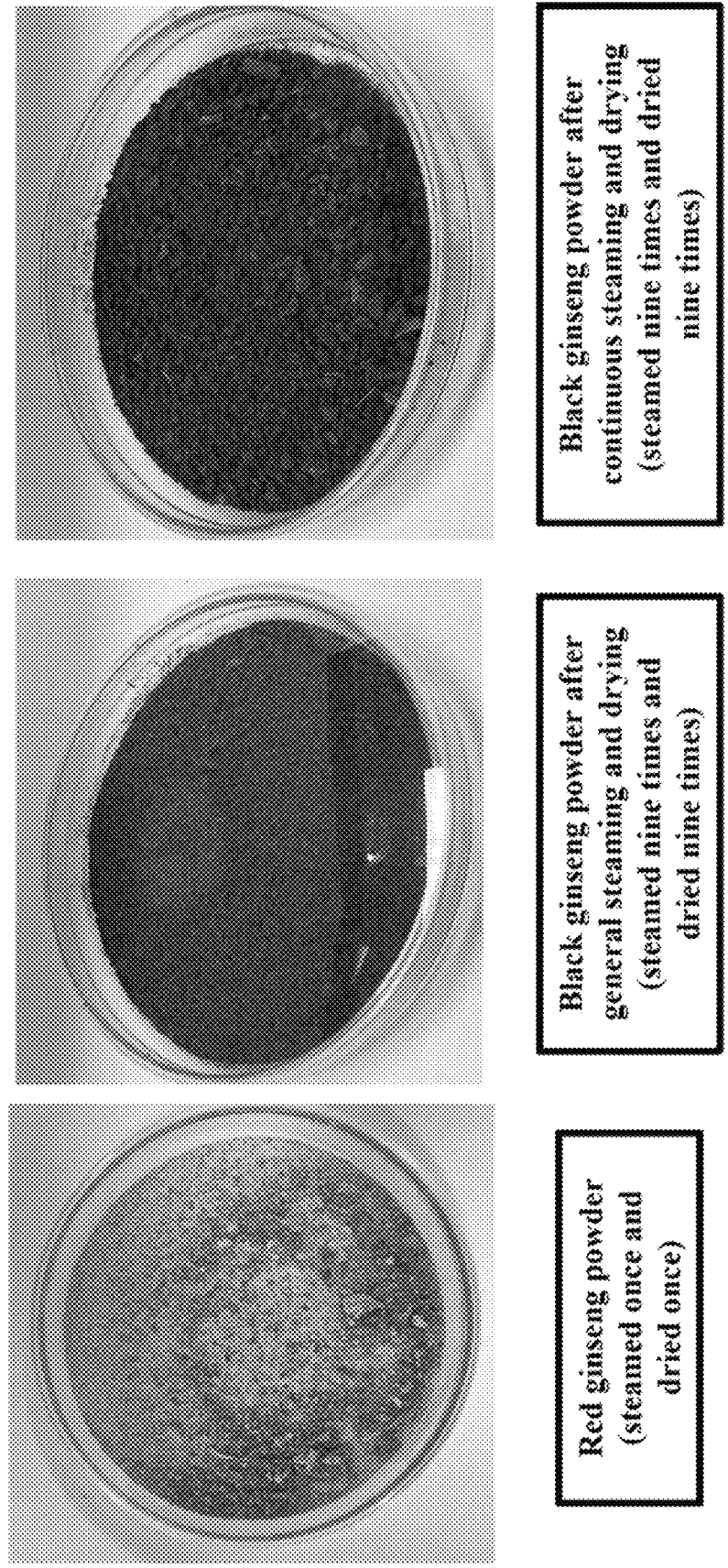
FIG. 6 is a photographic image in which red *ginseng* powder of the present invention, generally steamed and dried black *ginseng* powder, and continuously steamed and dried black *ginseng* powder are compared to one another.

In addition, moisture content in black *ginseng* and weight yield were compared between the different steaming methods. As a result, it was found that the moisture content is not much different when steaming-drying is carried out 9 times but the yield appears to be slightly higher when the continuous steaming dryer for preparing black *ginseng* is used (Table 7). It was also found that, from the crushed product obtained by crushing the black *ginseng*, stronger black color of continuously steamed and dried black *ginseng* powder is obtained (FIG. 6).

TABLE 7

Comparison between moisture content and weight yield depending on number of steaming-drying

| Number of steaming-drying | Moisture content (%) | | Weight yield (%) | |
|---|---|---|---|---|
| | General steaming-drying | Continuous steaming-drying | General steaming-drying | Continuous steaming-drying |
| 0 | 77 | 78 | 100 | 100 |
| 1 | 48 | 50 | 40 | 47 |
| 2 | 36 | 42 | 30 | 36 |
| 3 | 25 | 30 | 28 | 33 |
| 4 | 25 | 28 | 27 | 32 |
| 5 | 23 | 27 | 25 | 30 |
| 6 | 20 | 24 | 25 | 30 |
| 7 | 19 | 17 | 23 | 28 |
| 8 | 18 | 15 | 21 | 26 |
| 9 | 15 | 14 | 20 | 25 |

Example 3. Black *Ginseng* Ginsenoside Content

Ginsenoside content of black *ginseng*, which has been obtained by using either a general steaming method in which *ginseng* is typically steamed with a steamer, or the method of the present invention in which *ginseng* is steamed under supply of moisture by using continuous steaming-dryer for preparing black *ginseng*, is given in the Table 8.

As a result, it was found that sum of Rg3(S)+Rk1+Rg5 value is higher in 9 steaming-drying than 3 steaming-drying. In particular, the black *ginseng* obtained by using the continuous steaming dryer for preparing black *ginseng* of the present invention is higher by 69.75% than the black *ginseng* obtained by general steaming.

TABLE 8

Ginsenoside content (mg/g) in black ginseng

| Group | | Rg1 | Rb1 | Rg3(S) | Rk1 | Rg5 | Rg1 + Rb1 + Rg3(S) | Rg3(S) + Rk1 + Rg5 |
|---|---|---|---|---|---|---|---|---|
| Control | 1 Steaming-drying red ginseng | 1.19 | 3.24 | 0.09 | 0.06 | 0.05 | 4.52 | 0.19 |
| 3 Steaming-drying (including 1 steaming-drying of red ginseng) | General steaming black ginseng | 0.49 | 1.73 | 0.94 | 0.32 | 0.62 | 3.15 | 1.87 |
| | Continuous steaming black ginseng | 0.34 | 1.51 | 1.16 | 0.49 | 0.86 | 3.01 | 2.51 |
| | Increase rate (%) (Continuous/General) | −30.74 | −12.49 | 24.00 | 54.64 | 39.03 | −4.49 | 34.17 |
| 9 Steaming-drying (including 1 steaming-drying of red ginseng) | General steaming black ginseng | 0.00 | 0.14 | 1.17 | 0.39 | 0.79 | 1.31 | 2.35 |
| | Continuous steaming black ginseng | 0.00 | 0.08 | 1.82 | 0.76 | 1.40 | 1.90 | 3.99 |
| | Increase rate (%) (Continuous/General | 0.00 | −42.63 | 55.56 | 97.98 | 76.94 | 45.10 | 69.75 |

Example 4. Yield of Black *Ginseng* Concentrate and Ginsenoside Content Obtained by Different Concentration Methods Production efficiency and ginsenoside content of black *ginseng* concentrate concentrated by reduced-pressure concentration or plate type evaporative concentration are analyzed and the results are given in the following Table 9.

In case of the general reduced-pressure concentration, steam temperature becomes suddenly higher and the quality of concentrate is affected by the high temperature. However, according to the plate type evaporative concentration employed in the present invention, concentration can be achieved at relatively lower temperatures and it is not affected by the steam temperature. It was also found that the production efficiency is higher by 8 times or so in the present invention and, when the liquid extract is prepared as concentrate, concentration can be achieved without losing ginsenosides (Table 9).

TABLE 9

Comparison of concentration yield and ginsenoside content

| Item | | Liquid extract (20 Brix) | Concentrate (69 Brix) | | Theoretical content of ginsenosides at extract concentration |
|---|---|---|---|---|---|
| | | | Reduced-pressure evaporative concentration | Plate type evaporative concentration | |
| Concentration temperature (° C.) | | — | 65 to 70° C. | 55 to 60° C. | — |
| Exposure time affected by steam temperature | | — | 1 to 4 hours | None | — |
| Production efficiency (per concentrate volume/time) | | — | 300 kg/hr | 2,500 kg/hr | — |
| Ginsenoside content (mg/g) | Total of 3 kinds | 3.71 | 12.14 | 12.49 | 12.49 |
| | Rg3 | 1.29 | 4.34 | 4.45 | 4.45 |
| | Rg5 | 1.09 | 3.61 | 3.80 | 3.76 |
| | Rk1 | 1.24 | 4.09 | 4.24 | 4.28 |

Example 5. Sensory Test of Black *Ginseng* Concentrate

As for the sensory test, 40 adults as a test panel were asked to drink the black *ginseng* concentrates of Preparation example 1 or Comparative examples 1 to 4, each prepared by different production methods. The concentrate has been previously diluted to satisfy the individual's preference. Then, evaluation was made by the test panel in terms of malodor, bitter taste, and overall preference. For the evaluation, higher score is given for lower malodor and lower bitter taste, while, in case of the overall preference, higher score is given for more preferred concentrate. The evaluation was made based on 5-point scoring system.

TABLE 10

Sensory test of black ginseng concentrate prepared by various production methods

| Group | Malodor | Bitter taste | Overall preference |
|---|---|---|---|
| Preparation example 1 | 3.9 | 4.0 | 4.1 |
| Comparative example 1 | 3.3 | 3.4 | 3.3 |
| Comparative example 2 | 3.4 | 3.6 | 3.5 |
| Comparative example 3 | 3.7 | 3.7 | 3.8 |
| Comparative example 4 | 3.8 | 3.8 | 3.9 |

As a result, it was found that the black *ginseng* concentrate of Preparation example 1, which has been prepared by carrying out the steps of immersion in extract, continuous steaming-drying, plate type evaporative concentration, and heat treatment, is preferred more than the black *ginseng* concentrates of Comparative examples.

Example 6. Change in Ginsenosides after Continuous Heat Treatment

Ginsenoside content in black *ginseng* concentrate obtained by plate type evaporative concentration was compared among various heat treatment times for continuous heat treatment, and the results are given in the following Table 11.

TABLE 11

Ginsenoside content (mg/g) after heating black ginseng concentrate for various heating times

| Time for heat treatment | Rg3 Content | Rg3 Increase rate (%) | Rk1 Content | Rk1 Increase rate (%) | Rg5 Content | Rg5 Increase rate (%) | Total of 3 kinds Content | Total of 3 kinds Increase rate (%) |
|---|---|---|---|---|---|---|---|---|
| Control | 4.45 | — | 3.80 | — | 4.24 | — | 12.49 | — |
| 30 Minutes | 4.54 | 2.00 | 3.94 | 3.66 | 4.32 | 1.83 | 12.79 | 2.45 |
| 1 Hour | 4.54 | 2.13 | 3.95 | 3.90 | 4.41 | 4.11 | 12.90 | 3.34 |
| 2 Hours | 4.65 | 4.58 | 4.10 | 7.85 | 4.58 | 8.07 | 13.33 | 6.76 |
| 3 Hours | 4.84 | 8.80 | 4.32 | 13.79 | 4.81 | 13.43 | 13.97 | 11.89 |
| 4 Hours | 5.14 | 15.57 | 4.62 | 21.60 | 5.20 | 22.61 | 14.96 | 19.80 |
| 6 Hours | 5.75 | 29.25 | 5.34 | 40.59 | 5.94 | 40.12 | 17.03 | 36.39 |

Figure 7:
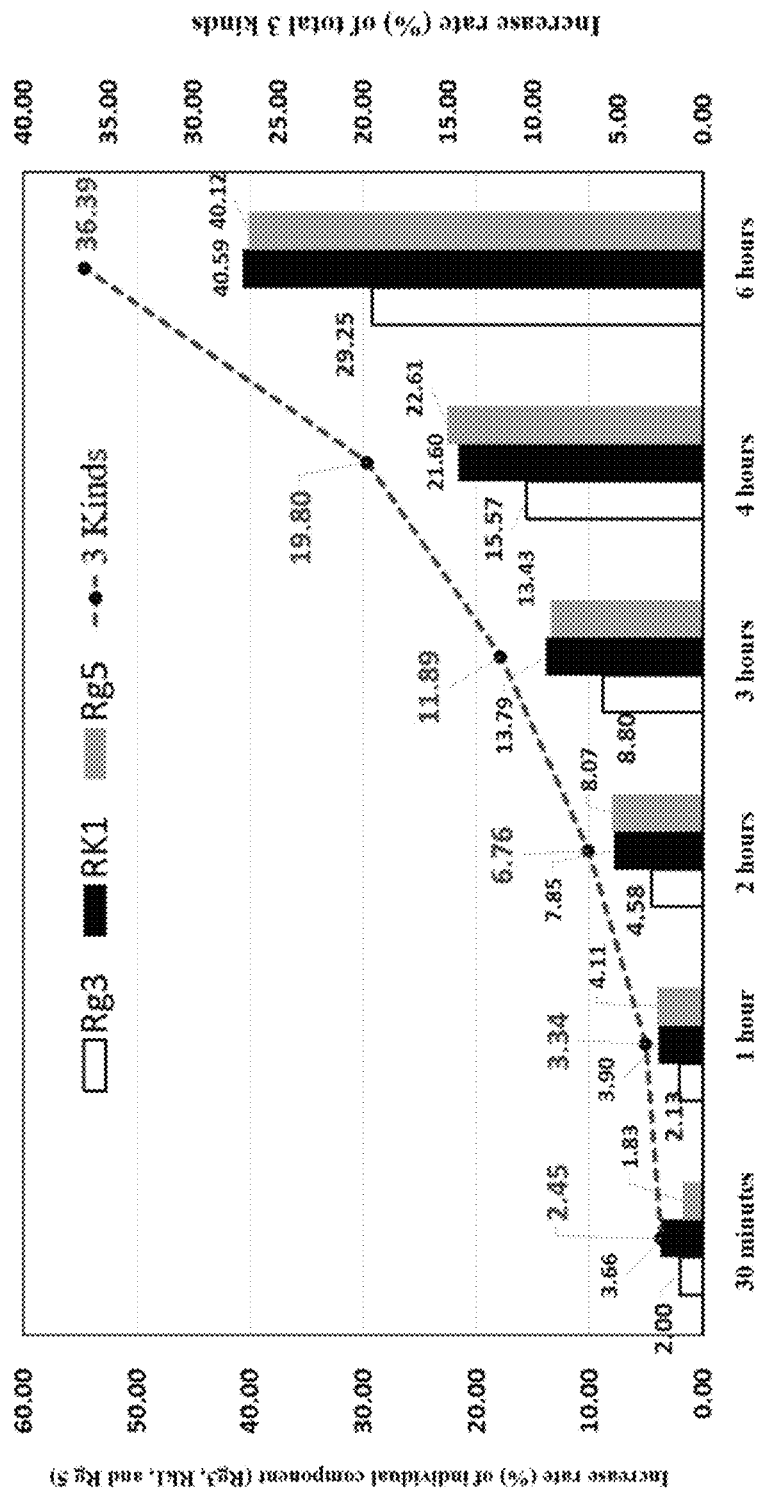
FIG. 7 is a graph for comparing the ginsenoside content in black *ginseng* concentrate depending on various times of continuous heat treatment.

As a result, it was found that all of Rg3, Rk1, and Rg5 have the highest content when the heat treatment is carried out for 6 hours (FIG. 7).

What is claimed is:

1. A method for producing black *ginseng* concentrate, the method comprising:
   (1) steaming *ginseng* followed by drying to prepare red *ginseng*;
   (2) carrying out extraction by adding water to a black *ginseng* mixture containing black *ginseng*, *Patrinia scabiosaefolia* roots, *Persicaria hydropiper* leaves, and *Persicaria thunbergii* leaves followed by filtration to prepare a mixed plant extract;
   (3) having the red *ginseng*, which is prepared in the step (1), immersed for 2 to 4 hours in the mixed plant extract prepared in the step (2) followed by recovery-recovering the red *ginseng* from the extract;
   (4) placing the red *ginseng* recovered in the step (3) in a steaming dryer followed by steaming, cooling, and drying to prepare black *ginseng*;
   (5) carrying out extraction of crushed black *ginseng*, which is obtained by crushing the black *ginseng* prepared in the step (4), by adding alcohol followed by filtration to prepare a black *ginseng* extract; and
   (6) concentrating the black *ginseng* extract prepared in the step (5) by using an evaporative concentrator followed by heat treatment.

2. The method of claim 1, wherein the black *ginseng* mixture of the step (2) is a black *ginseng* mixture in which, based on the total weight of black *ginseng* mixture, 48 to 52% by weight of black *ginseng*, 18 to 22% by weight of *Patrinia scabiosaefolia* roots, 18 to 22% by weight of *Persicaria hydropiper* leaves, and 8 to 12% by weight of *Persicaria thunbergii* leaves are admixed with one another.

3. The method of claim 2, wherein the black *ginseng* concentrate is produced by a process comprising
   (1) steaming *ginseng* followed by drying to prepare red *ginseng*;
   (2) carrying out extraction by adding water in an amount of 7 to 9 times (v/w) a black *ginseng* mixture containing, based on the total weight of black *ginseng* mixture, 48 to 52% by weight of black *ginseng*, 18 to 22% by weight of *Patrinia scabiosaefolia* roots, 18 to 22% by weight of *Persicaria hydropiper* leaves, and 8 to 12% by weight of *Persicaria thunbergii* leaves followed by filtration to prepare a mixed plant extract;
   (3) having the red *ginseng*, which is prepared in the step (1), immersed for 2 to 4 hours at 45 to 55° C. in the mixed plant extract prepared in the step (2) followed by recovering the red *ginseng* from the extract;
   (4) placing the red *ginseng* recovered in the step (3) in a steaming dryer followed by repeating 7 to 9 times a process of steaming, cooling, and drying to prepare black *ginseng*;
   (5) carrying out extraction of crushed black *ginseng*, which is obtained by crushing the black *ginseng* prepared in the step (4), by adding alcohol followed by filtration to prepare a black *ginseng* extract; and
   (6) concentrating at 50 to 60° ° C. the black *ginseng* extract prepared in the step (5) by using an evaporative concentrator to a Brix value of 67 to 71 followed by heat treatment for 5 to 7 hours at 85 to 95° C.

4. The method of claim 3, wherein the black *ginseng* concentrate is produced by a process comprising:
   (1) steaming *ginseng* for 1 to 3 hours at 90 to 110° C. and drying the steamed *ginseng* to obtain a red *ginseng* having moisture content of not more than 12 to 18% (v/w) at 45 to 55° C.;
   (2) carrying out extraction for 1 to 3 hours at 80 to 90° C. by adding water in an amount of 7 to 9 times (v/w) a black *ginseng* mixture containing, based on the total weight of black *ginseng* mixture, 48 to 52% by weight of black *ginseng*, 18 to 22% by weight of *Patrinia scabiosaefolia* roots, 18 to 22% by weight of *Persicaria hydropiper* leaves, and 8 to 12% by weight of *Persicaria thunbergii* leaves followed by filtration to prepare a mixed plant extract;
   (3) having the red *ginseng*, which is prepared in the step (1), immersed for 2 to 4 hours at 45 to 55° C. in the mixed plant extract prepared in the step (2) followed by recovering the red *ginseng* from the extract;
   (4) placing the red *ginseng* recovered in the step (3) in a steaming dryer followed by repeating 7 to 9 times a process of steaming, cooling, and drying to prepare black *ginseng*;
   (5) carrying out extraction for 1 to 3 hours at 55 to 60° C. of crushed black *ginseng*, which is obtained by crushing the black *ginseng* prepared in the step (4), by adding 60 to 80% (v/v) alcohol in an amount of 7 to 9 times (v/w) the crushed black *ginseng* followed by filtration to prepare a black *ginseng* extract; and
   (6) concentrating at 50 to 60° ° C. the black *ginseng* extract prepared in the step (5) by using an evaporative concentrator to a Brix value of 67 to 71 followed by heat treatment for 5 to 7 hours at 85 to 95° C.

5. The method of claim 4, wherein the black *ginseng* of the step (4) is prepared by, after adding the red *ginseng* to a steaming dryer, repeating 7 to 9 times the following process of steaming, cooling, and drying including:

maintaining the red *ginseng* for 60 to 90 minutes at temperature of 50 to 55° ° C. and humidity of 90 to 95%;

steaming the red *ginseng* for 4 to 8 hours at temperature of 90 to 95° C. and humidity of 90 to 95%;

cooling the steamed red *ginseng* for 60 to 90 minutes at humidity of 90 to 95% to temperature of 45 to 55° C., then cooling for 60 to 90 minutes at humidity of 90 to 95% to temperature of 25 to 30° C.; and drying at 50 to 55° C. while no moisture is supplied to the steaming dryer.

6. Black *ginseng* concentrate prepared by the method of claim 1.

\* \* \* \* \*